United States Patent
Banas et al.

(10) Patent No.: US 8,642,027 B2
(45) Date of Patent: Feb. 4, 2014

(54) COMPOSITIONS AND METHODS FOR MODULATING ISCHEMIC INJURY

(75) Inventors: Richard A. Banas, Turtle Creek, PA (US); David L. Steed, Pittsburgh, PA (US); Randall G. Rupp, Swanton, VT (US)

(73) Assignee: Stemnion, Inc., Pittsburgh, PA (US)

( * ) Notice: Subject to any disclaimer, the term of this patent is extended or adjusted under 35 U.S.C. 154(b) by 0 days.

(21) Appl. No.: 13/199,291

(22) Filed: Aug. 25, 2011

(65) Prior Publication Data

US 2012/0052045 A1 Mar. 1, 2012

Related U.S. Application Data

(60) Provisional application No. 61/402,596, filed on Sep. 1, 2010.

(51) Int. Cl.
*A61K 45/00* (2006.01)

(52) U.S. Cl.
USPC ...................................... 424/93.1; 424/278.1

(58) Field of Classification Search
None
See application file for complete search history.

(56) References Cited

U.S. PATENT DOCUMENTS

| 8,221,741 B2 * | 7/2012 | Marshall et al. ........... 424/93.21 |
| 2006/0263337 A1 | 11/2006 | Maziarz et al. |
| 2010/0068180 A1 | 3/2010 | Marshall et al. |

FOREIGN PATENT DOCUMENTS

WO PCTUS2008000396 7/2008

OTHER PUBLICATIONS

Banas, R.A., et al, 2008, Human Immunology 69:321-328.
Ueta, M., et al., 2002, Clin Exp Immunol 129:464-470.
Williams, M.A., 2003, J Hematol & Stem Cell Res 12:757-758.
Agrawal, S., et al., 2003, J Hematol & Stem Cell Res 12:749-756.
Lu, L., et al., 2009, Internat Immunopharm 9:549-552.

* cited by examiner

*Primary Examiner* — Daniel C Gamett
(74) *Attorney, Agent, or Firm* — Linda O. Palladino; Gail M Kempler

(57) ABSTRACT

The invention is directed to methods of modulating ischemic injury in tissues and organs. The invention is further directed to methods of increasing time to ischemic injury in tissues and organs. Such methods utilize compositions comprising cells capable of modulating inflammatory responses, referred to herein as Inflammatory Response Modulating Cells (IRMCs). The IRMCs any be used directly or cell membranes derived from them may be used in practicing the methods of the invention. In addition, the IRMCs and IRMC membranes may be used alone or in combination with each other and/or in combination with various suitable active agents.

5 Claims, No Drawings

COMPOSITIONS AND METHODS FOR MODULATING ISCHEMIC INJURY

CROSS-REFERENCE TO RELATED APPLICATIONS

This application claims priority under 35 USC §119(e) to U.S. Provisional Application No. 61/402,596, filed Sep. 1, 2010, the contents of which is incorporated herein by reference in its entirety

FIELD OF THE INVENTION

The field of the invention is directed to methods of modulating ischemic injury in tissues and organs, including donor tissue and organs and intact tissue and organs. The field of the invention is further directed to methods of increasing time to ischemic injury in such tissues and organs. Such methods utilize compositions comprising cells capable of modulating inflammatory responses, referred to herein as Inflammatory Response Modulating Cells (IRMCs). The IRMCs any be used directly or cell membranes derived from them may be used in practicing the methods. In addition, the IRMCs and IRMC membranes may be used alone or in combination with each other and/or in combination with various suitable active agents.

DESCRIPTION OF RELATED ART

PCT/US2008/00396 describes extraembryonic cells and Amnion-derived Multipotent Progenitor (AMP) cells, and/or cell lysates and/or conditioned media derived therefrom, that are useful agents capable of treating HVG, GVHD, as well as other immune and/or inflammatory diseases and disorders (incorporated herein by reference).

Banas, R. A., et al, (Human Immunology (2008) 69, 321-328) describe the immunogenicity and immunomodulatory effects of amnion-derived multipotent progenitor cells (incorporated herein by reference).

Ueta, M., et al., (Clin Exp Immunol 2002; 129:464-470) describe the immunosuppressive properties of decellularized amniotic membrane (incorporated herein by reference).

U.S. Published Application No. 2006026337 discloses the immunomodulatory properties of multipotent adult progenitor cells, called MAPCs, and uses thereof (incorporated herein by reference).

Williams, M. (Journal of Hematotherapy & Stem Cell Research, 2003, 12:757-758) discusses the functional expression of HLA-G and whether it can be exploited for successful stem cell transplantation and engraftment (incorporated herein by reference).

Lu, L., et al., (Internat. Immunopharm. 2009; 9:549-552) report that in vitro induced $CD4^+$ $CD25^+$ $Foxp3^+$ Tregs attenuate hepatic ischemia-reperfusion injury (incorporated herein by reference).

BACKGROUND OF THE INVENTION

When organs are harvested for transplant, their blood supply is interrupted for various periods of time and they become ischemic organs and at normal physiologic temperatures, rapid cell death occurs (ischemic injury). In the transplant field, the standard for harvested organ preservation has been cold storage (called cold ischemic storage). Preserving the harvested organ at sub-physiologic temperature reduces cellular metabolism and slows the rate of organ cell death. The organ is generally perfused with and often immersed in solutions in an effort to further reduce damage to the cells.

Unfortunately, cold ischemic storage does not completely preserve organs and prevent ischemic injury. The three most critical problems associated with cold ischemic storage include the narrow window of time allowed for safe transport, the potential for organ damage even if the transport occurs within safe time limits, and the inability to test the organ for function after harvest, storage and transport. Although cold ischemic storage helps reduce the extent of ischemic injury, damage does occur and the more time that elapses, the more damage that occurs. And, if too much time elapses, the organ will become unusable. Even when an organ can be transplanted within the narrow time frame allotted for safe storage, the organ invariably suffers some degree of ischemic injury, which can contribute to sub-optimal outcomes in the recipient. Because transplant organs are preserved in a "non-functioning" state during cold ischemic storage they cannot be further evaluated to determine the functional status. Thus, it is virtually impossible to determine if the organ is suitable for transplant.

Clearly, a need exists for compositions and methods for storing harvested organs that can modulate, reduce or even prevent ischemic damage so that the organ remains useful and suitable for transplant. It is the object of the subject invention to provide such compositions and methods. In addition, many organs and tissues become ischemic as the result of injury, disease, surgery, etc. The methods and compositions of the invention are suitable for preventing, modulating, reducing, treating or ameliorating ischemic injury and increasing recovery from such injury in these tissues and organs, as well.

BRIEF SUMMARY OF THE INVENTION

It is an object of the instant invention to provide novel compositions and methods for preventing, modulating, reducing, treating or ameliorating ischemic injury to tissues and organs, including donor tissue and organs and intact tissue and organs. It is also an object of the instant invention to increase the time to ischemic injury in tissues and organs, including donor tissue and organs and intact tissue and organs. This is accomplished by administering compositions comprising cells called Inflammatory Response Modulating Cells (IRMCs) or cell membranes derived from IRMCs. IRMCs are cells that are capable of modulating, preventing or reducing the inflammatory response that occurs in such tissues and organs. By modulating, preventing or reducing the inflammatory response in these tissues and organs, the amount of ischemic injury in the tissue or organ is reduced. In tissues or organs destined for transplant, such treatment will cause them to be more likely to be suitable for transplant and more likely to function appropriately in the recipient. IRMCs include but are not limited to extraembryonic cells (herein referred to as EE cells), including but not limited to extraembryonic HLA-G positive cells (herein referred to as EHP cells) and Amnion-derived Multipotent Progenitor cells (herein referred to as AMP cells); Mesenchymal Stem Cells (herein referred to as MSCs), Sertoli cells, hepatic stellate cells, adult basal fibroblasts, donor matched unseparated bone marrow cells, donor matched splenocytes, embryonic stem cells (ES cells), hematopoietic stem cells (HSCs) and certain regulatory T cells (Tregs). It will be recognized by skilled artisans that any virtually any cell capable of modulating, preventing or reducing the inflammatory response is suitable for use in practicing the methods of the invention.

Accordingly, a first aspect of the invention is a method for modulating ischemic injury in tissues or organs comprising perfusing the tissue or organ with a composition comprising IRMCs or IRMC membranes or a combination of both.

A second aspect of the invention is a method for preventing ischemic injury in tissues or organs comprising perfusing the tissue or organ with a composition comprising IRMCs or IRMC membranes or a combination of both.

A third aspect of the invention is method for reducing ischemic injury in tissues or organs comprising perfusing the tissue or organ with a composition comprising IRMCs or IRMC membranes or a combination of both.

A fourth aspect of the invention is method for increasing the time to ischemic injury in tissues or organs comprising perfusing the tissue or organ with a composition comprising IRMCs or IRMC membranes or a combination of both.

In specific embodiments of aspects one-four, the IRMCs are EE cells, EHP cells, AMP cells, MSC, Sertoli cells, hepatic stellate cells, adult basal fibroblasts, donor matched unseparated bone marrow cells, donor matched splenocytes, embryonic stem cells (ES cells), hematopoietic stem cells (HSCs) or certain regulatory T cells (Tregs). In more particular embodiment the IRMCs are AMP cells.

In another specific embodiment, wherein the IRMCs are irradiated prior to use. In another specific embodiment, the IRMCs are cultured under hypoxic conditions prior to use.

In other specific embodiments of aspects one-four the IRMC membranes are EE cell, EHP cell, AMP cell, MSC, Sertoli cell, Hepatic Stellate cell, adult basal fibroblasts, donor matched unseparated bone marrow cells, donor matched splenocyte, embryonic stem cell (ES cell), hematopoietic stem cell (HSC) or certain regulatory T cell (Treg) membranes. In a particular embodiment the IRMC membranes are AMP cell membranes.

In other specific embodiments of aspects one-four the organ is a kidney, heart, lung, pancreas intestine or skeletal muscle.

In other specific embodiments of aspects one-four the IRMCs or IRMC membranes are perfused in combination with another active agent. In a specific embodiment the other agent is corticosteroids, cyclosporine, tacrolimus, sirolimus, methotrexate, azathiopine, mercatopurine, cytotoxic antibiotics, polyclonal antibodies, monoclonal antibodies, interferon, opioids, TNF binding proteins, mycophenolate, FTY720 or other cell types.

In another particular embodiment of aspects one-four the perfusion is cold perfusion.

Other features and advantages of the invention will be apparent from the accompanying description, examples and the claims. The contents of all references, pending patent applications and issued patents, cited throughout this application are hereby expressly incorporated by reference. In case of conflict, the present specification, including definitions, will control

DEFINITIONS

As used herein, the terms "a" or "an" means one or more; at least one.

As defined herein "isolated" refers to material removed from its original environment and is thus altered "by the hand of man" from its natural state.

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cells" or "EE cells" means a population of cells derived from the extraembryonic tissue.

As used herein, the term "EHP cells" means a population of cells derived from the extraembryonic tissue which have the characteristics of being HLA-G positive upon isolation, are MHC Class II negative, do not express the co-stimulatory molecules CD80 and CD86 and are not MAPCs as described in US Published Patent Application No. 20060263337.

As used herein, the term "Amnion-derived Multipotent Progenitor cell" or "AMP cell" means a population of epithelial cells that are derived from the amnion. In addition to the characteristics described above for EHP cells, AMP cells have the following characteristics. They have not been cultured in the presence of any non-human animal-derived substances or products, making them and cell products derived from them suitable for human clinical use. They grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion epithelial cells, from which AMP cells are isolated, will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods used herein provide improved compositions and populations of cells. AMP cells have previously been described as "amnion-derived cells" (see U.S. Provisional Application Nos. 60/666,949, 60/699,257, 60/742,067, U.S. Provisional Application Nos. 60/813,759, U.S. application Ser. No. 11/333,849, U.S. application Ser. No. 11/392,892, and PCTUS06/011392, each of which is incorporated herein in its entirety).

The term "composition of extraembryonic cells" as used herein includes the cells and compositions described in this application and in US2003/0235563, US2004/0161419, US2005/0124003, U.S. Provisional Application Nos. 60/666, 949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179, the contents of which are incorporated herein by reference in their entirety.

As used herein "inflammatory response modulating cells" or "IRMCs" means cells that are able to modulate, prevent or reduce an inflammatory response in a tissue, an organ, or in vitro. Non-limiting examples of IRMCs include but are not limited to EE cells, EHP cells, AMP cells, MSCs, Sertoli cells, hepatic stellate cells, adult basal fibroblasts, donor matched unseparated bone marrow cells, donor matched splenocytes, embryonic stem cells (ES cells), hematopoietic stem cells (HSCs), and certain regulatory T cells (Tregs).

As used herein, the term "plasma membrane" means the phospholipid bilayer structure that comprises the external boundary of a cell. Plasma membranes have an external or extracellular face and an internal or intracellular face. Each face has unique features and components (i.e. proteins) associated with it that give it its unique properties. In addition, adherent cells exhibit polarity, meaning the aspect of the cell that is attached to the basement membrane, called the basal face, has different features than the aspect of the cell that is adluminal, called the apical face.

As used herein "inflammatory response modulating cell membranes" or "IRMC membranes" means plasma membranes that have been obtain from IRMCs by any method known for obtaining plasma membranes from cells.

As used herein "irradiated cells" means cells which have been treated with approximately 2000 rads of radiation such that the cells are incapable of dividing.

As used herein, "hypoxic conditions" for culturing cells refers to culturing cells in conditions containing 5% or less oxygen.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the certain composition or process. By "no non-human animal-derived materials" is meant that the materials have never been in or in contact with a non-human animal body or substance so they are not xeno-contaminated. Only clinical grade materials, such as recombinantly produced human proteins, are used in the preparation, growth, culturing, expansion, storage and/or formulation of such compositions and/or processes.

As used herein, "specific activity" means the specific activity of IRMCs, and is determined by calculating a 50% inhibition dosage ($ID_{50}$). For example, using a standard allogeneic-antigen MLR, the 100% response is calculated by determining the PBMC responder response to a mismatched stimulator without addition of, for example, AMP cells. AMP cells are then titered into the MLR at 1:2 serial dilutions. The number of AMP cells required to half the 100% response is reported as the $ID_{50}$.

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

The term "cell product" or "cell products" as used herein refers to any and all substances made by and secreted from a cell, including but not limited to, protein factors (i.e. growth factors, differentiation factors, engraftment factors, cytokines, morphogens, proteases (i.e. to promote endogenous cell delamination, protease inhibitors), extracellular matrix components (i.e. fibronectin, etc.).

As used herein, the term "adjunctive" means jointly, together with, in addition to, in conjunction with, and the like.

As used herein, the term "co-administer" can include simultaneous or sequential administration of two or more agents.

As used herein, the term "syngeneic" means genetically identical members of the same species.

As used herein, the term "allogeneic" means variation in alleles among members of the same species.

As used herein, the terms "immunosuppressive drugs" or "immunosuppressants" are drugs that are used in immunosuppressive therapy to inhibit or prevent activity of the immune system.

As used herein, the term "GVHD" refers to graft versus host disease, which means the processes that occur primarily in an immunocompromised host when it is recognized as non-self by immunocompetent cells of a graft.

As used herein, the term "HVG" refers to host versus graft response, which means the processes which occur when a host rejects a graft. Typically, HVG is triggered when a graft is recognized as foreign (non-self) by immunocompetent cells of the host.

As used herein, the terms "inflammation" or "inflammatory response" means the reaction that occurs in affected cells and adjacent tissues in response to an injury, insult, abnormal stimulation caused by a physical, chemical, or biologic substance, or in response to ischemic conditions.

As used herein, the term "immune response" means the cells, tissues and protein factors (i.e. cytokines) involved in recognizing and attacking foreign substances within the body of an animal.

As used herein, "ischemia" means an insufficient supply of blood to a tissue or organ.

As used herein "cold ischemic time" means the time interval that begins when a harvested tissue, organ or body part is cooled with a cold perfusion solution after organ procurement surgery and ends when the tissue or organ is implanted into the recipient.

As used herein "warm ischemic time" means the time a tissue, organ, or body part remains at physiologic body temperature after its blood supply has been interrupted but before it is cooled or reconnected to a blood supply.

As used herein, the term "pharmaceutically acceptable" means that the components, in addition to the therapeutic agent, comprising the formulation, are suitable for administration to the patient being treated in accordance with the present invention.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

As used herein "subject" may mean either a human or non-human animal.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

IRMCs

A number of cell types have been shown to modulate, prevent or reduce inflammatory responses in various settings. Applicants term the cells having this property as Inflammatory Response Modulating Cells (IRMCs). The following is a brief description of non-limiting examples of IRMCs.

Mesenchymal Stem Cells (MSCs)—There are many studies which report on the immunomodulatory properties of MSCs. Reviews of the literature can be found in Le Blanc, K. (Cytotherapy 2003 5(6):485-9) and Kiss, J., et al., (Ory Hetil 2008 149(8):339-46) as well as numerous other review articles (each incorporated herein by reference). MSCs are currently under development as therapeutic agents (Osiris' Prochymal; Pluristem's PLX-1).

Sertoli Cells—Lim, H., et al., (J Heart Lung Transplantation 2009 28(1):72-78) report that Sertoli cells have immunomodulatory properties and that chemokine receptor 7 (CCR7) can optimize the systemic immunomodulatory effect by guiding Sertoli cells from the periphery to secondary lymphoid organs (incorporated herein by reference). Dufour, J. M., et al., (Immunol Invest 2003 32(4):275-297) report that Sertoli cells protect co-grafted allogeneic and xenogeneic pancreatic islets from immune destruction and reverse diabetes in immunocompetent and autoimmune animals (incorporated herein by reference).

Hepatic Stellate Cells—Jiang, G., et al., (Transplantation 2008 86(11):1492-1502) report liver stromal hepatic stellate cells act as professional antigen-presenting cells and preferentially expand $CD25^+$ $Foxp3^+$ Tregs, which may contribute to immune regulation in the liver (incorporated herein by reference). Chen, C-H., et al., (Hepatology 2006 44(5):1171-1181) report the in vivo immune modulatory activity of hepatic stellate cells in mice using an islet transplantation model. They found that co-transplanted hepatic stellate cells effectively protected islet allografts from rejection (incorporated herein by reference).

Adult Fibroblasts—Haniffa, M. A., et al., (J Immunol 2007 179:1595-1604) report that adult human fibroblasts ate potent immunoregulatory cells and are functionally equivalent to mesenchymal stem cells. They show that dermal fibroblasts inhibit allogeneic T cell activation by autologously derived cutaneous APCs and other stimulators (incorporated herein by reference).

Embryonic Stem Cells—Crisostomo, P. R., et al., (Am J Physiol Heart Circ Physiol 2008, 295:H1726-H1735) report that embryonic stem cells attenuate myocardial dysfunction and inflammation after surgical global ischemia via paracrine actions (incorporated herein by reference)

Regulatory T cells (Tregs)—Lu, L., et al., (Internat. Immunopharm. 2009; 9:549-552) report that in vitro induced $CD4^+$ $CD25^+$ $Foxp3^+$ Tregs attenuate hepatic ischemia-reperfusion injury by preventing proinflammatory cytokine expression following warm ischemia-reperfusion insult (incorporated herein by reference).

EHP cells, and in particular, AMP cells—have been found to suppress inflammatory responses even at relatively small amounts (see PCT/US2008/00396, incorporated herein by reference). Using the methods described herein for cell isolation, characterization and expansion, EHP cells, and in particular, AMP cells, can be used to modulate, prevent or reduce the inflammatory response that occurs in tissues and organs, including donor tissue and organs and intact tissue and organs, and which leads to ischemic injury.

Donor matched unseparated bone marrow cells, donor matched splenocytes and hematopoietic stem cells are also suitable for use in the methods of the invention.

In addition to the cells themselves, cell membranes from IRMCs, can be used to modulate, prevent or reduce the inflammatory response. Cell membranes may be prepared by several methods known in the art (see, for example, Membrane Isolation on Polylysine-coated Beads: Plasma Membrane from HeLa Cells. Carle M. Cohen, Douglas I. Kalish, Bruce S. Jacobson, and Daniel Branton. Journal of Cell Biology, Vol. 75, 1977, 119-134; Plasma Membranes of Mammalian Cells. J. De Pierre, M. Karnovsky. Journal of Cell Biology, Vol. 56, 1973, 275-303; Isolation of the Plasma Membrane from Corneal Endothelial Cells. Z. Suzanne Zam, James Cerda, Frank Polack. Invest. Ophthal. Vis. Sci., Vol. 19, Num. 6, 1980, 648-652; Biomembrane Protocols: Isolation and Analysis. Edited by John Graham and Joan Higgins. Methods in Molecular Biology, Vol 19, 1993 Humana Press, Inc. 59-83 (all incorporated herein by reference).

Once isolated and prepared, IRMC membranes may be characterized for identification of key membrane immunologic surface markers by, for example, standard immunohistochemistry.

In addition, the immunomodulatory mechanisms of IRMC membranes may be evaluated by MLR and co-culture of responding PBMCs to stimulation such as allo-antigen, mitogen, and recall antigen in the presence of different concentrations of IRMC membranes (for details, see PCT/US2008/00396 and Banas, R. A., et al, (Human Immunology (2008) 69, 321-328, each incorporated herein by reference in its entirety).

Various methods for isolating different types of IRMCs are known in the art. For example, isolating cells from the extraembryonic tissue, which may then be used to produce EE, are described in, for example, US2003/0235563, US2004/0161419, US2005/0124003, U.S. Provisional Application Nos. 60/666,949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179) (each incorporated herein by reference).

Identifying EHP cells—Once EE cells are isolated, it is necessary to identify which cells have the characteristics associated with EHP cells. For example, the cells are tested for the presence of HLA-G, the absence of MHC Class II antigens, and the absence of co-stimulatory molecules CD80 and CD86.

AMP cell compositions are prepared using the steps of a) recovery of the amnion from the placenta, b) dissociation of the epithelial cells from the amniotic membrane using a protease, c) culturing of the cells in a basal medium with the addition of a naturally derived or recombinantly produced human protein (i.e. human serum albumin) and no non-human animal protein; d) selecting AMP cells from the epithelial cell culture, and optionally e) further proliferation of the cells, optionally using additional additives and/or growth factors (i.e. recombinant human EGF). Details are contained in US Publication No. 2006-0222634-A1, which is incorporated herein by reference.

Culturing of the AMP cells—The cells are cultured in a basal medium. Such medium includes, but is not limited to, EPILIFE® culture medium for epithelial cells (Cascade Biologicals), OPTI-PRO™ serum-free culture medium, VP-SFM serum-free medium, IMDM highly enriched basal medium, KNOCKOUT™ DMEM low osmolality medium, 293 SFM II defined serum-free medium (all made by Gibco; Invitrogen), HPGM hematopoietic progenitor growth medium, Pro 293S-CDM serum-free medium, Pro 293A-CDM serum-free medium, UltraMDCK™ serum-free medium (all made by Cambrex), STEMLINE® T-cell expansion medium and STEMLINE® II hematopoietic stem cell expansion medium (both made by Sigma-Aldrich), DMEM culture medium, DMEM/F-12 nutrient mixture growth medium (both made by Gibco), Ham's F-12 nutrient mixture growth medium, M199 basal culture medium (both made by Sigma-Aldrich), and other comparable basal media. Preferably, the medium is IMDM highly enriched basal medium. Such media should either contain human protein or be supplemented with human protein. As used herein a "human protein" is one that is produced naturally or one that is produced using recombinant technology. In specific embodiments, the basal media is IMDM highly enriched basal medium and the human protein is human serum albumin at a concentration of at least 0.5% and up to 10%. In particular embodiments, the human serum albumin concentration is from about 0.5 to about 2%. The human serum albumin may come from a liquid or a dried (powder) form and includes, but is not limited to, recombinant human serum albumin, PLASBUMIN® normal human serum albumin and PLASMANATE® human blood fraction (both made by Talecris Biotherapeutics). In a most preferred embodiment, the cells are cultured using a system that is free of non-human animal products to avoid xeno-contamination.

Optionally, other factors are used. In one embodiment, human recombinant epidermal growth factor (hrEGF) at a concentration of between 0-1 µg/mL is used. In a preferred embodiment, the hrEGF concentration is around 10-20 ng/mL. All supplements are clinical grade.

In a specific embodiment, the following method is used to obtain selected AMP cells. The cells are plated into plastic tissue culture vessels (i.e. T75 flasks) immediately upon isolation from the amnion. After ~1-5 days, preferably ~1-3 days, and most preferably ~2 days in culture, non-adherent cells are removed from the plastic tissue culture vessel and discarded and the adherent cells are kept. This attachment of cells to a plastic tissue culture vessel is the selection method used to obtain the desired population of AMP cells. Adherent and non-adherent AMP cells appear to have similar cell surface marker expression profiles but the adherent cells have the advantage of possessing greater viability than the non-adherent population of cells and are thus the desired population of AMP cells. Adherent AMP cells are cultured until they reach ~13,000-700,000 cells/cm$^2$, preferably ~53,000-500,000 cells/cm$^2$ and most preferably ~120,000-300,000 cells/cm$^2$. At this point, the cultures are confluent or close to confluent. Suitable cells cultures will reach this number of cells between ~5-14 days, preferably between 5-9 days. Attaining this criterion is an indicator of the proliferative potential of the AMP cells and cells that do not achieve this criterion are not selected for further analysis and use. Once the AMP cells reach ~13,000-700,000 cells/cm$^2$, preferably ~53,000-500, 000 cells/cm$^2$ and most preferably ~120,000-300,000 cells/cm$^2$, they are removed from the plastic tissue culture vessel and cryopreserved. This collection time point is called p0.

In certain embodiments of the invention, the IRMC, for example, AMP cells, are irradiated and/or pre-cultured in hypoxic conditions prior to their use.

The compositions of the invention can be prepared in a variety of ways. For example, a composition useful in practicing the invention may be a liquid comprising an agent of the invention, i.e. IRMCs and/or IRMC membranes in solution, in suspension, or both (solution/suspension). The term "solution/suspension" refers to a liquid composition where a first portion of the active agent is present in solution and a second portion of the active agent is present in particulate form, in suspension in a liquid matrix. The liquid composition is preferably aqueous.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive. The IRMCs or IRMC membranes may be combined with, for example, University of Wisconsin solution (a normokalemic, intracellular colloid solution) or Histidine-Tryptophan-Ketoglutarate (HTK) solution, or any other solution known by skilled artisans in the tissue and organ transplantation fields.

The present invention provides pharmaceutical compositions of IRMCs cells, including AMP cells, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. Examples of suitable pharmaceutical carriers are described in "Remington's Pharmaceutical Sciences" by E. W. Martin, and still others are familiar to skilled artisans.

The invention also provides for an article of manufacture (i.e. a Perfusion Kit) comprising packaging material and a pharmaceutical composition of the invention contained within the packaging material, wherein the pharmaceutical composition comprises compositions of IRMCs and/or IRMC membranes. The packaging material comprises a label or package insert which indicates that the IRMCs and/or IRMC membranes can be used for perfusing tissues and organs, including donor tissue and organs for transplant and intact tissue and organs.

Once the IRMC compositions (IRMCs and/or IRMC membranes) are produced they may be used in combination with other agents. Examples of other agents include but are not limited to corticosteroids, cyclosporine, tacrolimus, sirolimus, methotrexate, azathiopine, mercatopurine, cytotoxic antibiotics, polyclonal antibodies, monoclonal antibodies (i.e. anti-T-cell receptor (CD23) and/or anti-IL2 receptor (CD25) antibodies), interferon, opioids, TNF binding proteins, mycophenolate, and/or FTY720.

IRMCs or IRMC membranes, alone or in combination with other agents, may be perfused into the tissue or organ. For harvesting of tissues or organs the IRMCs or IRMC membranes may be combined with various solutions or suspensions as described above or any other solution known by skilled artisans in the tissue and organ transplantation field. The perfused tissue or organ may then be packed in ice and transported under sub-physiologic temperature to transplant site.

One of skill in the art may readily determine the appropriate concentration, or dose, of the IRMCs, for example AMP cells, for perfusion. The skilled artisan will recognize that a preferred concentration or dose is one which produces a therapeutic effect, such as reducing ischemic injury, in an organ or tissue. For example, AMP cells are prepared at a concentration of between about $1\times10^7$-$1\times10^8$ cells/mL, preferably at about $2.5\times10^7$-$7.5\times10^7$ cells/mL, and most preferably at about $5\times10^7$ cells/mL. The volume of cell mixture administered will depend upon several variables such as the size of the organ or tissue to be perfused, how complex it's circulatory system is, etc. and can only be determined by the attending physician at time of use. The concentration or dose of IRMC cell membranes, for example AMP cell membranes, will likewise need to be empirically determined.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Preparation of an Exemplary IRMC Composition: AMP Cell Composition

Recovery of AMP Cells—

AMP cells were dissociated from starting amniotic membrane using the dissociation agents PXXIII. The average weight range of an amnion was 18-27 g. The number of cells recovered per g of amnion was about 10-15×10$^6$.

Method of obtaining selected AMP cells: Cells were plated immediately upon isolation from the amnion. After ~2 days in culture non-adherent cells were removed and the adherent cells were kept. This attachment to plastic tissue culture vessel is the selection method used to obtain the desired population of cells. Adherent and non-adherent AMP cells appear to have a similar cell surface marker expression profile but the adherent cells have greater viability and are the desired population of cells. Adherent AMP cells were cultured until they reached ~120,000-150,000 cells/cm$^2$. At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reach ~120,000-150,000 cells/cm², they were collected and cryopreserved. This collection time point is called p0. The AMP cells are used in an art-accepted animal model of organ transplantation or ischemic injury. The AMP cells may optionally be irradiated prior to their use. The AMP cells may be pre-cultured under hypoxic conditions prior to their use.

Example 2

Preparation of an Exemplary IRMC Membrane Composition: AMP Cell Membrane Composition AMP cell membranes are prepared by any one of several methods known in the art (see, for example, Membrane Isolation on Polylysine-coated Beads: Plasma Membrane from HeLa Cells. Carle M. Cohen, Douglas I. Kalish, Bruce S. Jacobson, and Daniel Branton. Journal of Cell Biology, Vol. 75, 1977, 119-134; Plasma Membranes of Mammalian Cells. J. De Pierre, M. Karnovsky. Journal of Cell Biology, Vol. 56, 1973, 275-303; Isolation of the Plasma Membrane from Corneal Endothelial Cells. Z. Suzanne Zam, James Cerda, Frank Polack. Invest. Ophthal. Vis. Sci., Vol. 19, Num. 6, 1980, 648-652; Biomembrane Protocols: Isolation and Analysis. Edited by John Graham and Joan Higgins. Methods in Molecular Biology, Vol 19, 1993 Humana Press, Inc. 59-83. Once prepared, the AMP cell membranes are characterized for identification of key membrane immunologic surface markers by, for example, standard immunohistochemistry. Once characterized, the AMP cell membranes are used in an art-accepted animal model of organ transplantation or ischemic injury.

Example 3

Use of an Exemplary IRMC Composition (AMP Cell Composition) and IRMC Membrane Composition (AMP Cell Membrane Composition) in Animal Models of Organ Transplantation The AMP cell and/or AMP cell membrane compositions are tested in animal models of organ transplant to evaluate their ability to prevent, modulate, reduce, treated or ameliorate ischemic injury in the harvested organ. Standard animal models of organ transplantation are found in the scientific literature as well as in "Handbook of Animal Models in Transplantation Research", Edited by Donald V. Cramer, Luis Podesta and Leonard Makowka, published in 1993 by CRC Press (incorporated herein by reference).

Example 4

Use of an Exemplary IRMC Composition (AMP Cell Composition) on Tissue Ischemia-Reperfusion Injury AMP cells are used as multipotent repair cells for ischemic tissue injuries. The AMP cells are pre-cultured under hypoxic conditions prior to transplantation. Such hypoxic treatment will improve their tissue regenerative potential. The experimental approach includes testing AMP cells in a hind limb ischemia model. This model utilizes a controlled tension tourniquet circumferentially around the proximal thigh of a mouse for 3 hours. Reperfusion is initiated by release of tension on the tourniquet. Immediately following reperfusion, AMP cells ($5-20 \times 10^5$/mouse) are injected into the left ventricle. Perfusion-restoration of blood flow is monitored by laser Doppler flow imaging. Immunohistochemistry and quantitative PCR are used to assess accelerated tissue neovascularization and angiogenesis.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A method for reducing ischemic injury in tissues or organs that have been harvested for organ transplant comprising the step of perfusing the harvested tissue or organ with a composition comprising Amnion-derived Multipotent Progenitor (AMP) cells.

2. A method for increasing the time to ischemic injury in tissues or organs that have been harvested for organ transplant comprising the step of perfusing the tissue or organ with a composition comprising Amnion-derived Multipotent Progenitor (AMP) cells.

3. The method of claim 1 or 2 wherein the AMP cells are irradiated prior to use.

4. The method of claim 1 or 2 wherein the AMP cells are cultured under hypoxic conditions prior to use.

5. The method of claim 1 or 2 wherein the AMP cells are perfused in combination with another active agent, wherein the other agent is selected from the group consisting of corticosteroids, cyclosporine, tacrolimus, sirolimus, methotrexate, azathiopine, mercatopurine, cytotoxic antibiotics, polyclonal antibodies, monoclonal antibodies, interferon, opioids, TNF binding proteins, mycophenolate, FTY720 and other cell types.

* * * * *